United States Patent [19]

Maestrone et al.

[11] 3,961,068

[45] June 1, 1976

[54] USE OF IPRONIDAZOLE IN COMBATTING *SPHAEROPHORUS NECROPHORUS* INFECTIONS

[75] Inventors: Gian Paolo Maestrone, Staten Island, N.Y.; Milan Mitrovic, Nutley, N.J.

[73] Assignee: Hoffmann-La Roche Inc., Nutley, N.J.

[22] Filed: Sept. 30, 1974

[21] Appl. No.: 503,560

[52] U.S. Cl. .............................................. 424/273
[51] Int. Cl.² ........................................ A61K 31/415
[58] Field of Search .................................... 424/273

[56] References Cited
UNITED STATES PATENTS 3,634,446  1/1972  Hoffer et al. ...................... 424/273

OTHER PUBLICATIONS

Maslukhin – Chem. Abst. vol. 70 (1969) p. 1197(b).

*Primary Examiner*—Sam Rosen
*Attorney, Agent, or Firm*—Samuel L. Welt; Bernard S. Leon; R. Hain Swope

[57] ABSTRACT

The use of ipronidazole and water-soluble, pharmaceutically acceptable salts thereof in the prevention and treatment of infections in domestic animals caused by *Sphaerophorus necrophorus* is described.

7 Claims, No Drawings

USE OF IPRONIDAZOLE IN COMBATTING *SPHAEROPHORUS NECROPHORUS* INFECTIONS

BACKGROUND OF THE INVENTION

The present invention affords a highly efficacious method for the prevention and treatment of infections wherein the causative organism is *Sphaerophorus necrophorus*, an anaerobic, gram negative bacillus. This organism has been demonstrated to be the causative agent of foot rot in cattle, sheep and goats, liver abscesses and calf diphtheria in cattle, necrotic pneumonia in swine, and necrotic rhinitis in sheep, cattle and swine, diseases which are economically damaging to the commercial raisers of these animals.

Ipronidazole is a known compound which chemically is 1-methyl-2-isopropyl-5-nitroimidazole. The preparation of this compound and its pharmaceutically acceptable acid addition salts are described in U.S. Pat. No. 3,634,446 which issued Jan. 11, 1972. In said patent, the compound is disclosed as possessing antiprotozoal and antihistomonal activity, particularly the latter. The compound is described as being especially active in the treatment of the histomonal infection known as turkey blackhead disease or enterohepatitis. Ipronidazole, however, is not recognized in the art as possessing antibacterial activity. Such activity cannot be imputed from U.S. Pat. No. 3,737,546 issued June 5, 1973, which teaches the use of ipronidazole in the prevention and treatment of swine dysentery wherein the causative organism is the large spirochete *Treponema hyodysenteriae*. Another patent, Japanese Pat. No. 7305024, describes mouthwash compositions containing as the active ingredient metronidazole, which is chemically related to ipronidazole and which chemically is 1-(2-hydroxyethyl)-2-methyl-5-nitroimidazole. Such compositions are described as possessing strong activity against oral anaerobes such as *Peptococcus, Veillonella, Bacteriodes, Fusobacterium* ad *Treponema*. The disclosure of the use of this compound locally as a mouthwash is not viewed as suggesting that ipronidazole would be highly efficacious systemically against *S. necrophorus* infections. A recent paper has suggested, on the basis of in vitro studies and very limited clinical work that metronidazole may be of value in treating infections wherein the causative organisms are obligately anaerobic bacteria. These limited disclosures are not viewed as suggesting that the active ingredient of the present invention is highly efficacious in the treatment of infections wherein the causative organism is *Sphaerophorus necrophorus*.

DETAILED DESCRIPTION OF THE INVENTION

According to the present invention, it has been discovered that ipronidazole or pharmaceutically acceptable salts thereof possess unexpectedly high activity in effecting both a cure and prophylaxis against infections in domestic animals, i.e., cattle, horses, sheep, swine, goats and the like, wherein *Sphaerophorus necrophorus* is the causative organism. The method of the invention is particularly concerned with conditions such as foot rot in cattle, sheep and goats, and liver abscesses in cattle. Ipronidazole is effective in the practice of the invention via oral administration in drinking water and feed and also via parenteral administration, i.e., subcutaneous, intramuscular, intravenous, intraperitoneal or intrarumen injection.

In accordance with the present invention, ipronidazole and pharmaceutically acceptable salts thereof have been found to prevent and effect a cure of *S. necrophorus* infections when administered in the feed at levels as low as 0.005% by weight. For effective control of *S. necrophorus* infections, ipronidazole can be administered ad libitum at feed or drinking water levels of from about 0.005% by weight to about 0.03% by weight, preferably at about 0.01% by weight to about 0.02% by weight. The preferred concentration will depend to some extent on the severity of the infection. Additionally, the method of the invention encompasses the therapeutic treatment of *S. necrophorus* infections via parenteral administration as will be described hereinafter.

The pharmaceutically acceptable salts of ipronidazole in accordance with the present invention include water-soluble acid addition salts with organic and inorganic acids. The preferred salts are those with pharmaceutically acceptable inorganic acids. Most preferred are the hydrochloride and the bisulfate.

The therapeutic compositions of the invention which can be orally administered to the animals can be prepared by directly forming a homogeneous admixture of ipronidazole with a commercial dry feed or ration or by initially forming a concentrate or premix by mixing the active compound with a suitable, non-toxic, edible carrier material. Suitable carrier materials include, for example, corn meal, germ meal or other cereals, soy flour, soya grits, seed meal, oyster shell flour, calcium silicate and the like and may additionally contain other compatible medicaments. A suitable premix can likewise be prepared by admixing the desired quantity of ipronidazole to a measured amount of commercial feed. Premixes in accordance with the invention can advantageously contain from about 1% by weight to about 99% by weight ipronidazole, preferably from about 1% to about 79% by weight, and most preferably about 11% by weight ipronidazole. Such premixes are readily mixed with the feed or ration by techniques conventional in the art.

Where parenteral therapy is contemplated in accordance with the present invention, a single dosage of from 10 mg. to 100 mg., preferably from about 25 mg. to 50 mg. of ipronidazole per kilogram of body weight of the animal to be treated is utilized. A significant response to such parenteral therapy has been demonstrated. The dosage regimen for such therapy will vary according to the age and type of animal, site of infection, severity of infection and the like. For most therapeutic situations, a single daily injection is required for up to 4 days. It has been demonstrated, however, that up to 10 days therapy may be required in the instance of a chronic or significantly advanced infection. Once a remission of symptoms has been observed, it is recommended that the animal as well as others in the herd with which there may have been contact be placed on a prophylactic or therapeutic diet. The extent of parenteral dosage and subsequent diet are considered to be within the discretion of the attending veterinarian.

Parenteral preparations suitable for the practice of the invention are preferably aqueous in nature due to the ability of the ipronidazole to form water-soluble acid addition salts with pharmaceutically acceptable acids. Such preparations may be in reconstitutable powder form and may contain adjunct materials conventional in the art of pharmaceutical compounding such as, for example, preservatives, stabilizers, salts for varying osmotic pressure, buffers and the like. Typical parenteral preparations contain a sufficient amount of a water-soluble acid addition salt of ipronidazole to provide from about 200 mg. to about 2500 mg., preferably from about 1000 mg. to about 1500 mg. of the free base per dose. Such preparations may be in single or multiple dose containers and may be administered intraruminally, intravenously or intraperitoneally.

The following examples further illustrate the invention.

EXAMPLE 1

A total of 6.04 grams of parenteral grade ipronidazole hydrochloride, equivalent to 5.0 grams of free base, was filled into an ampul utilizing a Diehl Meter electric filler or other suitable type filler. The ampuls were sealed and sterilized at 255°F. for 2 hours. Immediately before use this powder is solubilized by the addition of sufficient Water for Injection U.S.P. to achieve a final volume of 50 ml.

EXAMPLE 2

The following example illustrates typical feed supplements suitable for the prevention and treatment of *S. necrophorus* infections in accordance with the invention.

| Ingredient | Premix: 12/2% Grams/Kilogram |
|---|---|
| Ipronidazole | 125 |
| Microcel E (Calcium Silicate) | 50 |
| Pulverized Oyster Shell Flour | 825 |

PROCEDURE

The pulverized oyster shell flour was placed in a suitable mixer and, while mixing, the Microcel E was slowly added. After the addition of Microcel E was completed and with continued mixing the ipronidazole was slowly added after which mixing was continued until the mass was homogeneous. The addition of this premix to commercial feed at a rate of 1 ¾ pounds/ton yields a concentration of ipronidazole of 100 gm. per ton. Such commercial feeds may contain other nutritional or medicinal agents if such are compatible with ipronidazole.

| Ingredient | Premix: 22% Grams/Kilogram |
|---|---|
| Ipronidazole | 220 |
| Microcel E | 80 |
| Soy Oil | 10–50 |
| Soy meal run (toasted, extracted, milled soy) | 650–690 |

| Ingredient | Premix: 11% Grams/Kilogram |
|---|---|
| Ipronidazole | 110 |
| Microcel E | 40 |
| Soy Oil | 10–100 |
| Ground Rice Hulls | 750–840 |

PROCEDURE

A portion of the soy meal run (or ground rice hulls) was placed in a suitable mixer and about 10 grams (or 1% by weight of the final mixture) of the soy oil and the Microcel E slowly added thereto and the whole thoroughly mixed. The purpose of the oil is to minimize dust and maintain the mixture in a slightly moist condition during mixing. Therefore, sufficient oil is utilized to so maintain the mixture and the amount of soy meal run (or ground rice hulls) added to the mixture to bring it to final weight is adjusted in terms of the amount of oil utilized. The ipronidazole was then added with mixing and the whole thoroughly mixed until homogeneous. The required amount of additional grain was then added to bring the final weight of the mixture to 1 kilogram and the whole again mixed until homogeneous.

These premixes when combined with commercial feeds at the rate of 2 pounds per ton yield a concentration per ton of 200 mg. and 100 mg. ipronidazole, respectively.

EXAMPLE 3

The activity of ipronidazole against *S. necrophorus* was demonstrated in vitro as follows: A 48-hour bacterial growth of various strains of *S. necrophorus* was swabbed onto the surface of 5% bovine blood Mueller-Hinton agar plates on which 6.3 mm discs, containing 2.0 mcg. ipronidazole were placed. The plates were then incubated under anaerobic conditions at 37°C. for 48 hours. The diameter of the zone of inhibition around the disc was then measured and is expressed in millimeters. The results are set forth in the following table.

Table

| Compound | Disc Potency (mcg.) | Zone of Inhibition (diameter in mm) Strain of *S. necrophorus* | | | |
|---|---|---|---|---|---|
| | | 675-1 | 676 | 677 | 679 |
| Ipronidazole | 2.0 | > 25 | > 25 | > 25 | > 25 |

In vivo tests were conducted as follows:

Male, albino mice weighing approximately 20 grams were inoculated in the plantar area of the posterior foot with a 0.1 ml. inoculum of *S. necrophorus* virulent culture, propagated for 48 hours in thioglycolate medium and properly titrated ($7.1 \times 10^8$ organism). This inoculation produces a severe degree of significant local pathology but is not lethal. Groups of 10 mice demonstrating such pathology were given a single subcutaneous injection of various dosages of ipronidazole 1 day after infection. The minimum effective dose was calculated to be 25 mg/kg. The effectiveness of this dosage was 95% 7 days post inoculation and 98% 14 days post inoculation based on remission of characteristic pathology when compared to infected untreated controls.

Groups of 10 mice, similarly dosed with organism, were fed various levels of ipronidazole in the feed beginning 24 hours pre-infection and 1 hour past infection, respectively. The feed in each instance was continued for 7 days. Observations were made at the termination of medication (7 days) and 7 days thereafter. The results are expressed in Table 1 below in terms of a percent efficiency where 100% efficiency is a complete absence of lesions.

Table I

| % Concentration of Ipronidazole in Feed | Percentage Efficiency | | | |
|---|---|---|---|---|
| | Treatment Begun 24 hrs. pre-infection | | Treatment Begun 1 hr. post-infection | |
| | Day 7 | Day 14 | Day 7 | Day 14 |
| 0.03 | 98 | 100 | 95 | 96 |
| 0.02 | * | * | 95 | 98 |
| 0.01 | 90 | 94 | * | * |
| 0.005 | 86 | 90 | 89 | 93 |

Table I-continued

| % Concentration of Ipronidazole in Feed | Percentage Efficiency | | | |
|---|---|---|---|---|
| | Treatment Begun 24 hrs. pre-infection | | Treatment Begun 1 hr. post-infection | |
| | Day 7 | Day 14 | Day 7 | Day 14 |
| 0.0025 | 43 | 40 | 72 | 82 |
| 0.00125 | 17 | 0 | 33 | 11 |

*Test not conducted with this concentration

The results given above indicate that ipronidazole is highly effective in doses ranging from 0.03% to about 0.005% by weight in the feed.

Other groups of mice were inoculated into the hepatic parenchyma and caudal part of the chest cavity, respectively. Both the hepatic and thoracic infections were fatal to all animals in unmedicated control groups. In the thoracic infections, ipronidazole was administered in various concentrations in the feed beginning 1 day prior to infection to demonstrate prevention and the day of infection to demonstrate treatment. In both instances medication was continued for 7 days post infection. Those animals surviving were observed at 7 and 14 days for evidence of clinical signs and at 14 days were sacrificed and examined for lung lesions. The results are set forth in Table II wherein clinical signs, etc., are expressed in terms of percent each group.

Table II

Ipronidazole in Feed
S. necrophorus (Strain 675)

| Prevention | | % Concentration in Feed | | | |
|---|---|---|---|---|---|
| | | 0.02 | 0.01 | 0.005 | 0.0* |
| 7 days post infection | % mortality | 17 | 14 | 28 | 75 |
| | % clinical signs | 0 | 0 | 28 | 0 |
| 14 days post infection | % mortality | 17 | 14 | 28 | 75 |
| | % clinical signs | 17 | 28 | 28 | 12 |
| | % lung lesions | 20 | 17 | 20 | 50 |
| Therapy | | | | | |
| 7 days post infection | % mortality | 33 | 55 | 80 | 75 |
| | % clinical signs | 11 | 11 | 0 | 0 |
| 14 days post infection | % mortality | 33 | 55 | 80 | 75 |
| | % clinical signs | 11 | 22 | 0 | 12 |
| | % lung lesions | 17 | 25 | 50 | 50 |

S. necrophorus (Strain 677)

| Prevention | | % Concentration in Feed | | | |
|---|---|---|---|---|---|
| | | 0.02 | 0.01 | 0.005 | 0.0* |
| 7 days post infection | % mortality | 0 | 0 | 0 | 0 |
| | % clinical signs | 11 | 22 | 20 | 55 |
| 14 days post infection | % mortality | 0 | 0 | 0 | 0 |
| | % clinical signs | 11 | 11 | 0 | 44 |
| | % lung lesions | 11 | 11 | 20 | 89 |
| Therapy | | | | | |
| 7 days post infection | % mortality | 10 | 0 | 0 | 0 |
| | % clinical signs | 30 | 30 | 20 | 55 |
| 14 days post infection | % mortality | 10 | 0 | 0 | 0 |
| | % clinical signs | 20 | 40 | 40 | 44 |
| | % lung lesion | 33 | 40 | 60 | 89 |

*Infected, untreated controls

In the liver infection, medication was initiated 1 day prior to infection and continued for 7 days thereafter. The surviving mice were observed after 7 and 14 days post infection for clinical signs and were sacrificed at 14 days and observed for liver lesions. The results are set forth in Table III wherein mortality, clinical signs, etc., are expressed in terms of a percent of each group.

Table III

Ipronidazole in Feed

| Days Post Medication | Percent | Concentration in Feed | | | |
|---|---|---|---|---|---|
| | | 0.02 | 0.01 | 0.005 | 0.0* |
| S. necrophorus | | | | | |
| Strain 675-1 | | | | | |
| 7 | Mortality | 0 | 0 | 30 | 20 |

Table III-continued

Ipronidazole in Feed

| Days Post Medication | Percent | Concentration in Feed | | | |
|---|---|---|---|---|---|
| | | 0.02 | 0.01 | 0.005 | 0.0* |
| | Clinical signs | 0 | 30 | 40 | 80 |
| 14 | Mortality | 20 | 40 | 50 | 80 |
| | Clinical signs | 20 | 30 | 20 | 0 |
| | Liver lesions | 12 | 33 | 20 | 0 |
| Strain 676 | | | | | |
| 7 | Mortality | 0 | 20 | 20 | 80 |
| | Clinical signs | 0 | 10 | 30 | 20 |
| 14 | Mortality | 0 | 50 | 80 | 100 |
| | Clinical signs | 10 | 20 | 0 | — |
| | Liver lesions | 0 | 20 | 0 | — |
| Strain 677 | | | | | |
| 7 | Mortality | 0 | 0 | 0 | 0 |
| | Clinical signs | 0 | 0 | 20 | 80 |
| 14 | Mortality | 0 | 0 | 0 | 0 |
| | Clinical signs | 20 | 40 | 20 | 80 |
| | Liver lesions | 0 | 25 | 20 | 80 |
| Strain 679 | | | | | |
| 7 | Mortality | 0 | 10 | 10 | 0 |
| | Clinical signs | 20 | 30 | 10 | 20 |
| 14 | Mortality | 0 | 10 | 10 | 0 |
| | Clinical signs | 0 | 10 | 20 | 0 |
| | Liver lesions | 0 | 0 | 20 | 70 |

*Infected, untreated controls

The effectiveness of ipronidazole in combatting the above described experimentally induced infections is clearly demonstrated by the data in the Tables.

Four goats weighing 35.5, 54.5, 44.5 and 95 kilograms, respectively, with naturally occurring foot rot were treated for 10 days with ipronidazole. Three were treated with 25 mg/kg. of the drug administered by intravenous, intraperitoneal and intraruminal administration, respectively. The fourth goat received 50 mg/kg/day ipronidazole via intraruminal injection. Throughout the trial, the rumination of the goats appeared normal as did the color and consistency of the feces. Blood counts taken before and after the trial were within normal limits. The drug was well tolerated. On the fifth day of treatment, the lameness and swelling of the foot had disappeared. At the termination of the trial, no clinical evidence remained to indicate the presence of the infection and all interdigital necrotic ulcers initially present were healed.

We claim:
1. A method for the treatment of infections in domestic animals wherein the causative organism is *Sphaerophorus necrophorus* which comprises orally administering to an animal afflicted therewith feed or drinking water containing from about 0.005% by weight to about 0.03% by weight of a substance selected from the group consisting of ipronidazole and pharmaceutically acceptable acid addition salts thereof.
2. The method of claim 1 wherein said drinking water or feed contain from about 0.01% by weight to about 0.02% by weight of said substance.
3. The method of claim 1 wherein said substance is ipronidazole and administration is via the feed.
4. The method of claim 1 wherein said substance is ipronidazole hydrochloride and administration is via the drinking water.
5. A method for the therapeutic treatment of infections in domestic animals wherein the causative organism is *Sphaerophorus necrophorus* which comprises parenterally administering to animals afflicted therewith a composition containing from about 10 mg. to about 100 mg. of a substance selected from the group consisting of ipronidazole and pharmaceutically acceptable salts thereof per kilogram of body weight of said animal.
6. The method of claim 5 wherein said composition contains from about 25 mg. to about 50 mg. of said substance per kilogram of body weight of said animal.
7. The method of claim 5 wherein said substance is ipronidazole hydrochloride.

* * * * *